United States Patent
Pail

[19]

[11] Patent Number: 5,810,736
[45] Date of Patent: Sep. 22, 1998

[54] WRIST PULSE MONITOR

[76] Inventor: Opher Pail, 595 Main St., New York, N.Y. 10044

[21] Appl. No.: 518,033

[22] Filed: Aug. 22, 1995

[51] Int. Cl.[6] ........................................................ A61B 5/00
[52] U.S. Cl. ........................... 600/500; 600/503; 600/480
[58] Field of Search .................................. 128/690, 700, 128/706, 633, 664–667, 687; 600/500–503, 479, 480

[56]  References Cited

U.S. PATENT DOCUMENTS

| | | |
|---|---|---|
| 3,426,747 | 2/1969 | Herman et al. . |
| 4,083,366 | 4/1978 | Gombrich et al. ...................... 128/690 |
| 4,120,296 | 10/1978 | Prinz . |
| 4,224,948 | 9/1980 | Cramer et al. ........................... 128/690 |
| 4,252,128 | 2/1981 | Kane ....................................... 128/690 |
| 4,295,472 | 10/1981 | Adams .................................... 128/690 |
| 4,406,290 | 9/1983 | Walbeoffe-Wilson et al. ......... 128/690 |
| 4,409,983 | 10/1983 | Albert ..................................... 128/690 |
| 4,425,921 | 1/1984 | Fujisaki et al. . |
| 4,685,464 | 8/1987 | Goldberger et al. . |
| 4,915,116 | 4/1990 | Hasebe et al. . |
| 4,971,062 | 11/1990 | Hasebe et al. .......................... 128/664 |
| 5,065,749 | 11/1991 | Hasebe et al. .......................... 128/664 |
| 5,243,992 | 9/1993 | Eckerle et al. .......................... 128/690 |
| 5,301,154 | 4/1994 | Suga . |
| 5,313,940 | 5/1994 | Fuse et al. . |
| 5,431,170 | 7/1995 | Mathews ................................. 128/633 |

*Primary Examiner*—Robert L. Nasser
*Attorney, Agent, or Firm*—Felfe & Lynch

[57] ABSTRACT

A pulse monitor is provided which has a pulse monitor unit supported on a wrist band over the carpal tunnel, with a infra-red optical sensor which picks up the flow of blood therein. The detected blood flow is transmitted by a radio frequency transmitter to a display unit also supported on the wrist of the user, which processes the data signal and displays a pulse. Alternate embodiments provide for separate wrist bands supporting the pulse detector and the display unit, and for a combined detector and display unit, as well as multiple optical sensors.

19 Claims, 3 Drawing Sheets

5,810,736

WRIST PULSE MONITOR

FIELD OF THE INVENTION

This invention relates to devices for taking the pulse of a user, and more particularly to devices whereby a user may monitor his own pulse.

DESCRIPTION OF THE PRIOR ART

In the prior art, heartbeat monitors are provided to users, particularly people who suffer from heart disease, to allow them to regulate the speed of their exercise or other activity to obtain the optimum pulse for their respective condition.

In some prior art devices, the user's pulse is detected by a sensor strap around the user's chest. This strap may communicate with a wrist watch monitor, either by cable as is shown in U.S. Pat. No. 4,425,921 (FIG. 4) or by a radio transmitter. Such a system, however, presents some problems. For instance, the chest strap is uncomfortable to wear, and may not be usable for some people, especially women, for anatomical reasons. In addition, the communication of the radio signal from the chest just to the wrist watch is of sufficient distance that it may present some difficulty in the reliable transmission of the signal.

Other types of devices have been proposed wherein the wrist watch contains a sensor which is used to estimate the pulse of the user and display it on the watch. One example of this type of device is U.S. Pat. No. 4,120,296 to Prinz. This system presents a number of drawbacks, especially from the standpoint of manufacturing. The sensor is mounted in the band to detect the pulse from the inside of the wrist. The sensor is connected to a wire which passes through the band and into the body of the watch itself.

The difficulty of that apparatus is that the entire apparatus must be purchased as a custom-manufactured unit, because a band with a wire is not readily available. Furthermore, it is normally desirable to have a watch body which is sealed, and the extension of the wire from the band into the body of the watch itself compromises the seal effect. Furthermore, the unified nature of the apparatus does not permit the user to change the strap of the watch should it be become damaged or for some other reason, since the entire object is a unified system. Additionally, the location of the sensor is not in the optimal position on the inside of the wrist to best detect the pulse of the user.

SUMMARY OF THE INVENTION

It is therefore an object of the invention to provide a reliable wrist pulse monitor which can be comfortably used by virtually anyone, which permits use of a sealed watch and a band of a type that is commonly available. It is also an object of the invention to provide a pulse sensor in a location which allows for superior pulse detection.

Accordingly, the present invention provides a pulse monitor system which comprises a pulse detector unit and a display unit. The pulse detector unit has an optical sensor supported on a wrist of the user which sensors the volume of blood passing through the wrist and is connected with a wireless signal transmitter which receives a signal from the optical sensor and transmits a wireless signal derived from this signal. The display unit has a band structure which secures it on the wrist, and it includes a display device supported on the band structure. The display device includes a receiver which receives the wireless signal from the transmitter of the pulse detector unit, and a signal processing circuit which takes the signal received and displays a numerical pulse value derived from this signal on the watch display.

Other objects and advantages of the invention herein will become apparent from the specification herein, and the scope of the invention will be articulated in the claims.

DETAILED DESCRIPTION OF THE DISCLOSURE

Figure 1:
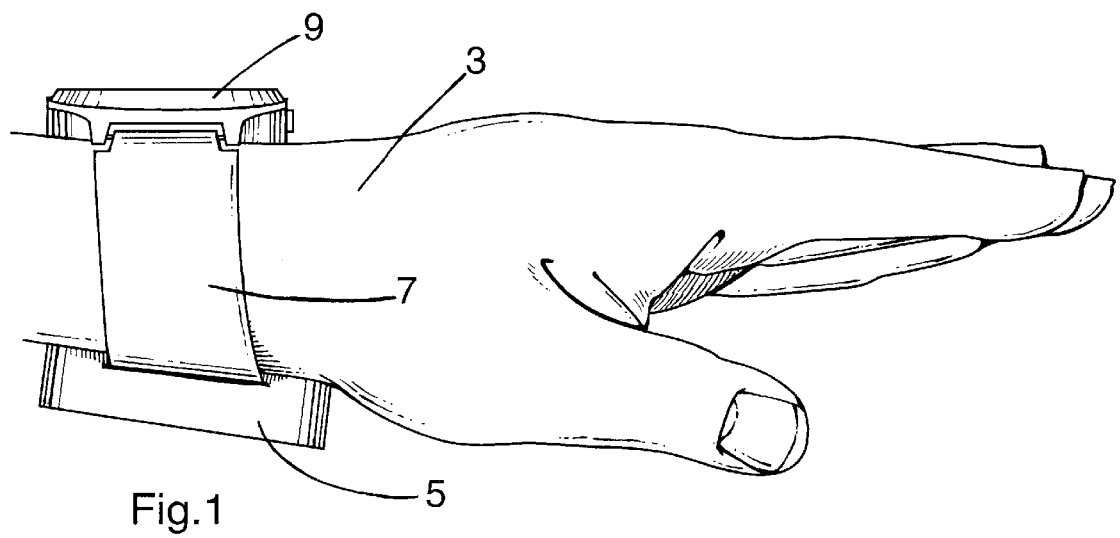
FIG. 1 is an elevational view the apparatus of the present invention applied to the hand of the user.

As best shown in FIG. 1, the preferred embodiment of the present invention comprises two units applied to the wrist 3 of a user. The pulse detector unit 5 is secured over the inside part of wrist 3 by band 7. A watch display unit 9 is secured on the outside part of the wrist on the same wrist band 17. The band may be of leather, nylon webbing, or virtually any other suitable material, including elastic material. Securement around the wrist may be by any means known in the art, such as by a buckle, snaps, Velcro®, etc. In the preferred embodiment, the band passes through a securement slot 10 in the body pulse detector unit 5.

Figure 3:
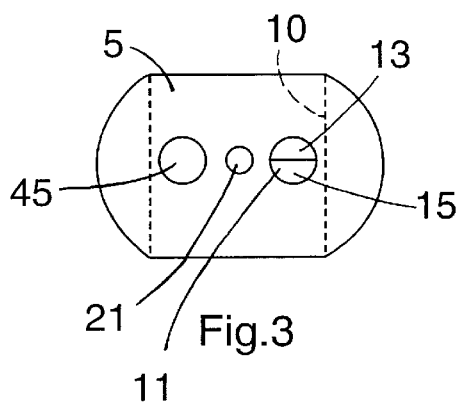
FIG. 3 is a view of the side of the pulse detector unit faces the user's wrist.

Referring to FIG. 3, the pulse detector unit 5 is provided with an inward facing optical sensor system 11. Source 13 generates an infra-red light from which the warm blood passing through the wrist 3 is optically detected by infra red optical detector 15. Sensor system 11 is most preferably a reflective sensor which combines an infra red light source 13 with a high sensitivity photo transistor, i.e., optical detector 15. Such as infra red sources and phototransistors are well known in the art.

Figure 2:
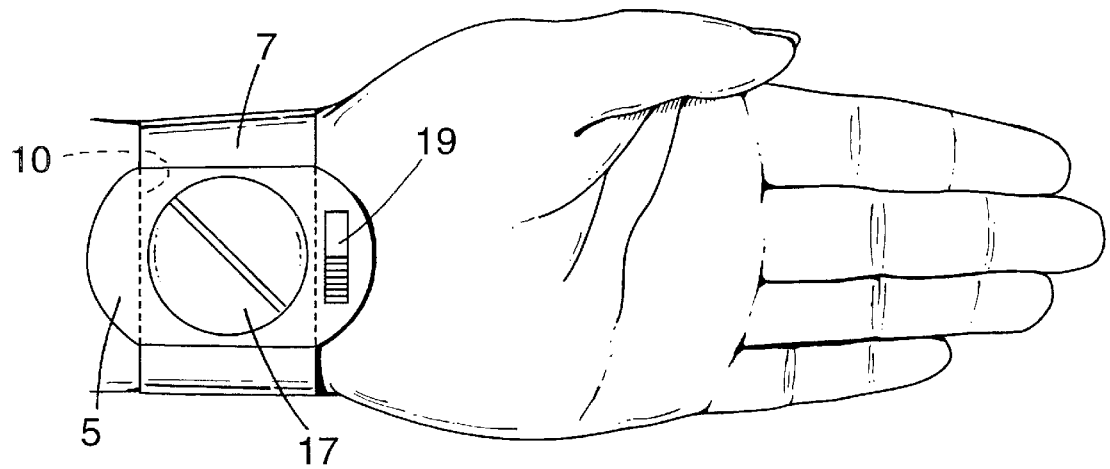
FIG. 2 is a bottom view of FIG. 1, showing the pulse detector unit of the present invention.

As best shown in FIG. 2, band 7 is configured so that, when properly secured on the wrist, the sensor 11 overlies the carpal tunnel of the wrist. In this position, the sensing of movement of the blood is particularly good, because the vessels supplying blood to the hand converge to pass through the center of the articulation of the wrist, and closer to the inside surface of the wrist, making optical observation most effective.

The pulse detector unit 5 is powered by a battery which is placed in the body of the detector unit 5 through an opening closed by securement cover 17. To preserve the battery when the pulse detector unit is not in use, a switch 19 is provided which allows the user to turn off the sensor mechanism. An alternative switch is provided on the face of the pulse detector unit which faces the inside of the wrist. This switch 21 projects towards the wrist from the surface 23 of the pulse detector unit 5. When the pulse detector unit 5 is strapped onto the wrist, switch 21 is pressed down, and the pulse detector unit 5 switched on, deriving power from the battery. When the pulse detector unit is removed from the wrist, this allows switch 21 to pop up, switching off the pulse detector unit 5 and preserving the energy of the battery.

Figure 4:
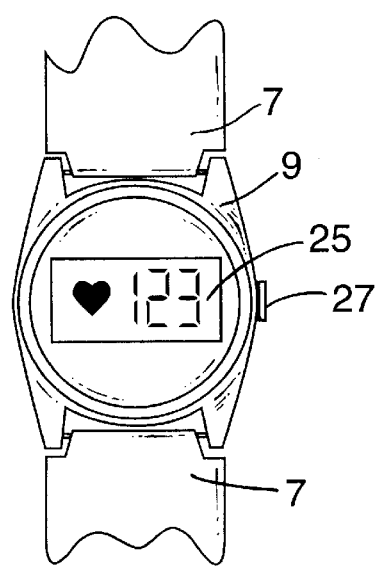
FIG. 4 is a view of the display unit watch of the invention.

The wristwatch display unit 9 is best shown in FIG. 4. Display unit 9 is equipped with an LCD display 25 which shows numerical values. The display unit 9 may be provided with one or more control buttons 27 which can change the type of display from pulse indication to normal watch operation, or stop watch or otherwise adjust the functioning of the display unit 9.

Figure 5:
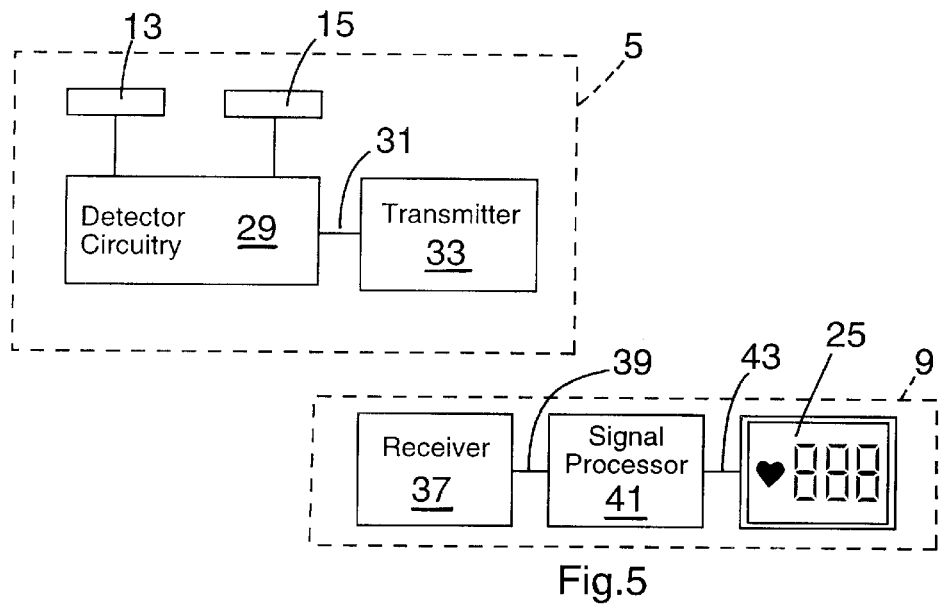
FIG. 5 is a schematic showing the circuitry of the present invention.

FIG. 5 shows the schematic of the preferred embodiment. The optical detector unit 5 contains detector circuitry 29 connected with the light emitter 13 and the light detector 15. Responsive to readings of the blood detected by the light detector 15, the optical circuitry produces an electrical signal transmitted along line 31 to transmitter 33.

Transmitter 33 may be any transmitter of a wireless signal, such as, e.g., a electromagnetic or radio signal transmitter. Transmitter 33 is most preferably a frequency modulated (FM) radio frequency transmitter which transmits an FM signal corresponding to the signal received along line 31. This radio signal, generally indicated at 35, preferably has a frequency generally in the range of 45 to 50 megahertz, and most preferably about 49 megahertz, pursuant to FCC regulation, part 15 is analogous to cordless phone radio transmission. However, again, virtual any method of wireless transmission may be used, such as, e.g., electromagnetic transmission under 5 kHz. This is especially appropriate because the distance the signal must travel (through the wrist) is quite short.

The signal 35 is received by a radio receiver 37 in display unit 9. This receiver 37 receives the radio signal 35 and transmits a corresponding electrical signal along line 39 to signal processor 41. Signal processor 41 processes the signal received from line 39 and outputs a signal, either serially or in parallel, along a transmission line 43 to LCD display 25.

The signal transmitted along line 39 is an analog signal, and the signal processor 41 serves to analyze this raw data, which represents the infra-red optical readout of blood passing through the wrist of the user, converting the data to a digital numerical pulse value to be output at through line 43.

The signal processor 41 performs a number of steps which yield this digital pulse signal. The raw blood flow data is first converted into a raw pulse digital data signal by timing of the period necessary for a pre-selected number of pulses to appear in the raw pulse data signal. The signal processor 41 determines the time T that the number of pulses took, and divides the number K of pulses by the time T to generate a raw pulse digital data signal indicative of the pulse of the individual, i.e., Pulse=K/T.

This raw digital data signal is then filtered and smoothed. The filtering process occurs in two steps. In the first filtering step, the raw pulse is compared to maximum and minimum values which represent the possible physiological limiting values of the pulse, as for example, a minimum value of 25 and a maximum value of 250. If the value of the raw pulse digital data signal falls outside of these limits, the signal is disregarded, and the signal processor waits for the next raw pulse data signal. If the raw pulse data signal falls between the minimum and maximum permitted values, the raw pulse data signal is then subjected to a second filter step.

The second filter step compares the current raw pulse signal value with the value of the last previous pulse signal, which is stored in the processor circuit. If the difference between these successive pulse signals exceeds a reasonable range for a human, i.e., if the current pulse signal indicates that the pulse has changed by too large a jump in value, the current pulse signal is viewed as unreliable and is discarded, and the signal processor 33 awaits the next signal. The suitable threshold value for detecting an error based on the change in the pulse rate between successive readings varies with on the physiological condition of the user. An athlete may exhibit great changes in heart rate during training, while a heart patient has a more regular pattern of heart rates. The change limit value may be input by the user through controls such as button 27 on display unit 9 as a sensitivity coefficient. or as one of a group of parameters set by selecting one of several operational modes based on various conditions of the user.

If the raw pulse signal is between the minimum and maximum permitted values, and if it has not deviated from the last previous pulse data signal by an amount beyond the change limit value, the pulse signal is then viewed as a reliable one and is subjected to a smoothing algorithm. The smoothing algorithm may be one of many well known in the art, but particularly preferred is a smoothing algorithm in which a percentage of the current pulse data signal is combined with a percentage of the last previous pulse signal displayed. The coefficients here may range from 25% of the prior signal pulse and 75% of the present signal pulse to 75% prior signal pulse and 25% of the present signal pulse.

These parameters can also vary depending on the physiological condition of the user and the type of activity, since there are exercise programs wherein the pulse of the individual fluctuates a great deal, and those wherein it changes only very slightly over time. When an exercise program is used in which the pulse is expected to fluctuate greatly, less smoothing is desirable because the user will be provided with the most relevant current data. On the other hand, should an exercise program be used in which a steady pulse rate is expected, more smoothing is desirable, because it produces a more uniform and predictable pulse reading. The display unit 9 may be adjustable by the user so that a specific combination of filtering parameters is selected based on the user's condition.

The signal derived after the filtering and smoothing steps is transmitted to the LCD display 25 by line 43. In the preferred embodiment, this signal is digital, so it may be transmitted serially or in parallel as is well known in the art.

The optical detector unit 5 is optionally provided with a second sensor 45, which may be of an optical type such as sensor system 11, or of some other type known in the art. A data signal from this second sensor 45 may be picked up and correlated with the data signal from sensor system 11 to improve the accuracy of the sensor.

It will be understood that a variety of calculations can be done using with the value of the pulse. Accordingly, the watch display unit 9 may also include circuitry which can log the pulse rates for an exercise period, or produce error messages or other notices to the user based on either detection of a large amount of erroneous data or on specific parameters of the pulse which is detected.

Figure 6:
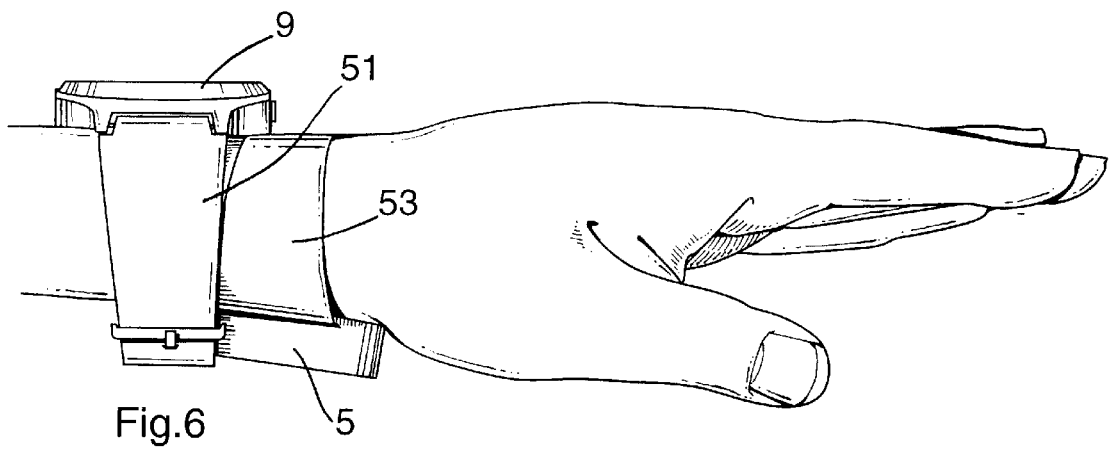
FIG. 6 is an elevational view of an alternate embodiment of the invention herein.

FIG. 6 shows an alternate embodiment of the invention. In the alternate embodiment, display unit 9 and pulse detection unit 5 are each supported on separate respective wrist bands 51 and 53. The structure of the pulse detection unit itself is the same of that of the pulse detection unit 5 shown in the embodiment of FIGS. 1 to 5. Wrist band 53 supports the pulse detection unit so that the sensor system thereof lies over the carpal tunnel.

The display unit 9 is preferably one with band 51 on the same wrist as the pulse detector unit 5, but may also be worn on the other wrist from the pulse detector unit 5. In such an application, the power of the radio transmitter may have to be greater than in the preferred embodiment to ensure that communications between the wrist and the user are maintained. This system nevertheless continues to provide the advantage of having a pulse detector that does not rely on a chest strap which, as was discussed previously, may not be readily worn by certain users.

Figure 7:
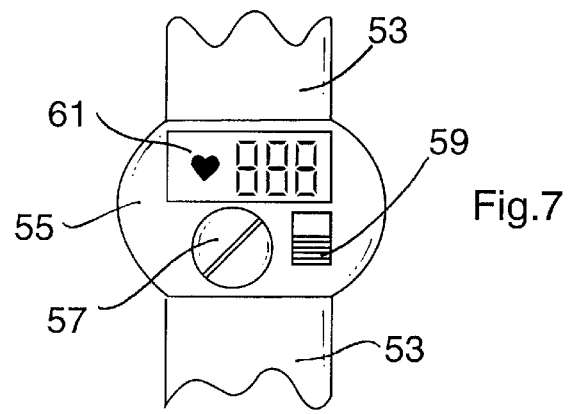
FIG. 7 is a bottom view as in FIG. 2 of a further alternate embodiment of the invention.

A further alternative embodiment is shown in FIG. 7. In this embodiment, a pulse detector unit 55 is supported on strap 53. The structure of the pulse detector unit 55 on the side facing the wrist is the same as that of pulse detector unit 5, best shown in FIG. 3, and a sensor system 11 and switch 21 are supported on the inward face of unit 55. The outside part of the pulse detector unit 55 is provided with a battery opening 57, a switch 59 by which the operator can switch off the battery power, and a display 61 which operates similarly to display 25 in the wrist display device.

The internal circuitry of the embodiment shown in FIG. 7 is similar to that of the embodiment of FIGS. 1 to 5, except that the conductor 31 in the pulse detector unit 5 connects directly to line 39 of the display circuitry 9. Since the entire unit is contained in one wrist mounted device, there is no need for a transmitter or a receiver. However, the filtering and smoothing of the raw pulse data signal by signal processor 33 is performed as has been described above, and the resulting pulse signal is displayed in numerical form by LCD display 61.

Figure 8:
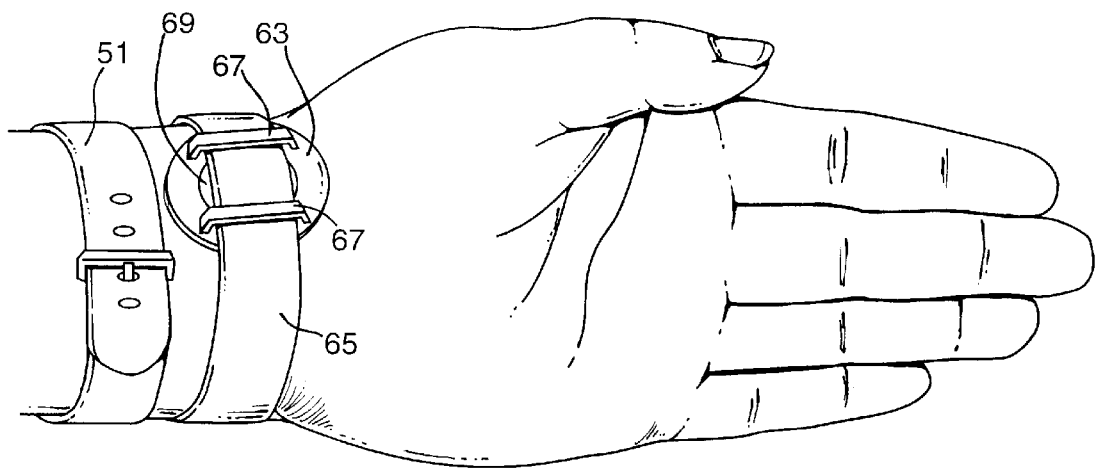
FIG. 8 is a view as in FIG. 1 of a further alternate embodiment of the invention.
Figure 9:
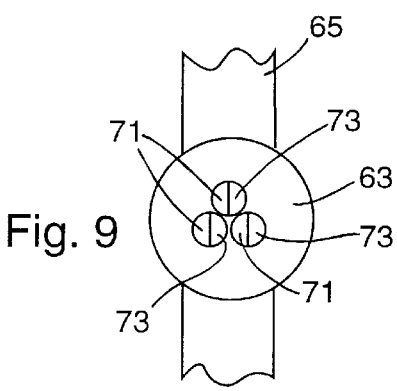
FIG. 9 is a view of the detector of FIG. 8 showing the side facing the wrist of the user.
Figure 10:
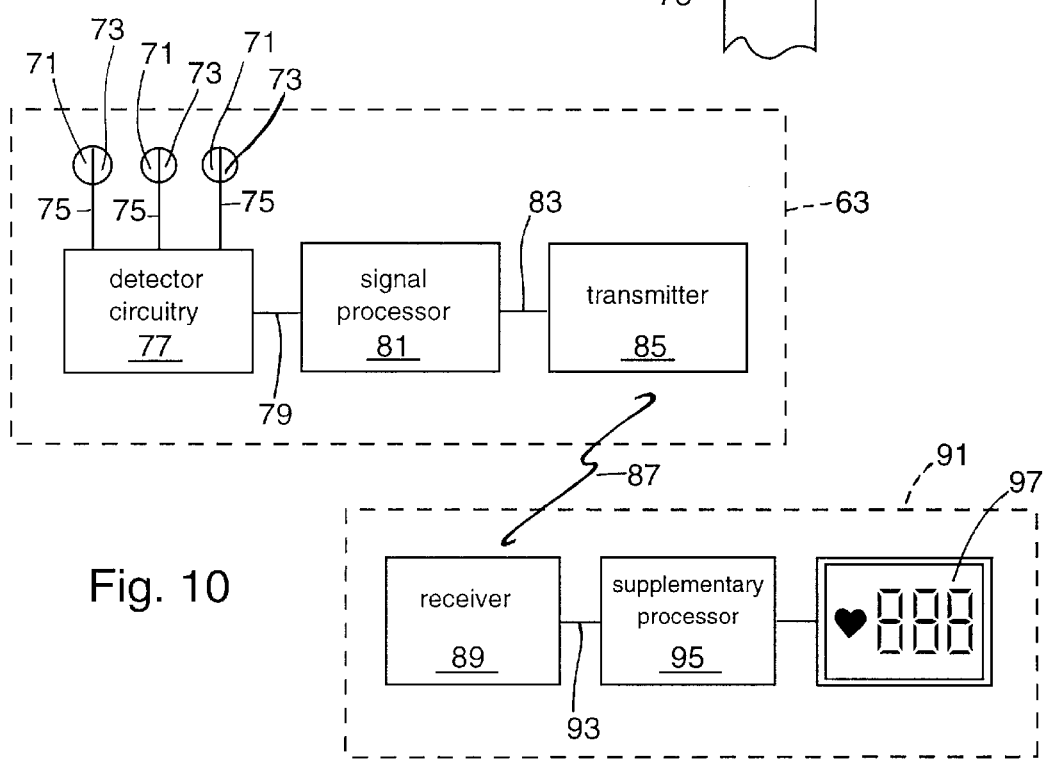
FIG. 10 is a schematic of the alternate embodiment of FIG. 8 and 9.

FIGS. 8, 9 and 10 show a further alternate embodiment of the pulse monitor of the invention. As in the embodiment of FIG. 6, the embodiment of FIG. 8 has a display unit and a detector unit 63 each mounted on respective wrist bands 51 and 65. Strap 65 is secured to detector unit 63 by passing underneath brackets 67. Detector 65 has an access opening 69 for inserting a battery to power the apparatus. Optionally, a switch (not shown) may be provided to switch the power off when the apparatus is not in use.

As best shown in FIG. 9, the side of the detector unit 63 facing the wrist of the user is equipped with three optical detector systems, each comprising a light emitter 71 and light detector 73. As in the other embodiments, the light emitters 71 are preferably infra red light sources, and the light detectors 73 are preferably phototransistor sensitive to infra red. These emitters and detectors are grouped together in a closely grouped pattern and are configured so that when the detector unit 63 is placed on the wrist, all three of these sensor systems overlie the pulse area on the wrist of the user, which can generally be described as a triangle defined by a line extending to the thumbward side from the meridian of the wrist and along the crease of articulation of the wrist.

The schematic of the pulse detection system of FIGS. 8 and 9 is shown in FIG. 10. Each of the optical detection unit is connected with detector circuitry which controls the operation of the detectors, and receives raw optical pulse data therefrom along lines 75. The detector circuitry 77 transmits the broad data signals to the fruit of line 79 to signal processor 81.

Signal processor 81 analyzes the data received from the three optical detectors 73. Initially, as has been discussed above with respect to the preferred embodiment, the signal processor filters the raw pulse data from these optical detectors 73 by eliminating or disregarding pulses which are outside the expected range of values, or which have shown an improper rapid change of pulse. The surviving signals may be averaged, or there statistical methods may be used to determine the most reliable of the three sets of pulse data which are received from the optical detector 73, such as a standard deviation based on recent historical pulse data to delete the less reliable data. The most reliable pulse data figure is transmitted as a signal along line 83 to transmitter 85. Transmitter 85, as in the preferred embodiment, is a wireless signal transmitter, preferably a radio frequency transmitter.

Signal 87 is transmitted by transmitter 85, and received by a receiver 89 in display unit 91. Display unit 91 is similar in appearance to display unit 9 of the embodiment shown in FIG. 1, being a wrist-watch type display. The signal received by receiver 89 is transmitted through line 93 to an optional supplementary processor 95. The supplementary processor 95 may add various data or calculations to the raw pulse data, such as comparisons with earlier data regarding the user, warning messages or indications that activity should be increased in speed, etc. The supplementary processor 95 transmits this data as well as the best pulse data to display 97 where the pulse data and any other relevant information is displayed to the user through an LCD or other display.

It will be understood that this multiple optical detector unit 63 may be equipped with a display such as in an embodiment of FIG. 7 instead of the transmitter 85. In such a case, there is no need for the user to wear a wrist watch, and the pulse may be read off of the outer surface of the display unit supported on the outer surface of the detector unit 63.

The terms used herein should be viewed as terms of description rather than of limitation since those skilled in the art with the specification before them will be able to make modifications thereto without departing from the spirit of the invention herein.

Wherefore I claim:

1. A pulse monitor system for displaying the pulse of a user, said system comprising:

a pulse detector unit having
an optical sensor adapted to be supported on a wrist of the user and sensing varying amount of blood passing through said wrist and generating a sensor signal responsive to said sensing, and a wireless signal transmitted receiving said sensor signal from said optical sensor and transmitting a wireless signal derived from said optical sensor signal; and a display unit adapted to be supported on one of the wrists of the user and comprising a band structure adapted to secure said display unit on said one of the wrists of the user and a display device supported on said band structure, said display device including
a receiver receiving said wireless signal from said wireless signal transmitter and generating a received signal corresponding thereto,
a display circuit receiving said received signal and displaying a numerical pulse to the user derived from said received signal; and
said display circuit having a signal processing circuit deriving a pulse signal from the received signal,
said signal processing circuit processing said pulse signal to yield a display pulse signal, said signal processing circuit:
a) interrupting the pulse signal when the numerical value thereof is below a preselected minimum or above a preselected maximum;
b) interrupting the pulse signal when the change in numerical value of said pulse signal from the previous value of the pulse signal exceeds a preselected value; and c) smoothing the values of said pulse signal.

2. The invention according to claim 1 and said optical sensor comprising three sensor elements supported adjacent each other in a generally triangular pattern, and each sensing blood in said wrist.

3. The invention according to claim 2 and said pulse detector unit being adapted to be supported so that the optical sensor is over a portion of said wrist adjacent the crease of articulation of the wrist and to the thumbward side of the meridian of the wrist.

4. The invention according to claim 3 and said display unit and said pulse detector unit being maintained in proximity to each other when the units are both supported on the same wrist of the user.

5. The invention according to claim 1 and said wireless signal being a frequency modulated radio signal.

6. The invention according to claim 1 and said display unit and said pulse detector unit being maintained in proximity to each other when the units are both supported on the same wrist of the user.

7. The invention according to claim 1 and said pulse detector unit including a second band structure adapted to secure said pulse detector unit on said wrist.

8. The invention according to claim 1 and said display circuit including an LCD display field structure displaying said pulse value.

9. The invention according to claim 1 and said pulse detector unit having a battery supplying power thereto and a switch adapted to close when the pulse detector unit is placed on the wrist, causing flow of electricity from the battery to power the pulse detector unit.

10. The invention according to claim 1 and said pulse detector unit being supported on the band structure of the display unit.

11. A pulse monitor system for displaying the pulse of a user comprising:

a pulse detector unit comprising at least two optical sensors, a signal processing circuit connected with said optical sensors, and a transmitter connected with said signal processing circuit;

said pulse detector unit being adapted to be supported on the wrist of the user so that the optical sensors overlie a portion of the wrist of the user adjacent to the crease of the wrist and to the thumbward side of the meridian of the wrist, said optical sensors each detecting varying amounts of blood in the wrist and each generating a respective first signal, said signal processing circuit processing said first signals and transmitting a second signal to the transmitter, said second signal being derived from said first signals by selecting the most reliable pulse data available therefrom;

said transmitter generating a wireless signal corresponding to said second signal data; and a display unit comprising a band adapted to be securingly engaged on one of the wrists of the user, and a display device supported on the band;

said display device comprising a signal receiver receiving said wireless signal and generating a third signal corresponding thereto;

a signal display circuit receiving said third signal and generating therefrom a display signal; and a display receiving said display signal and displaying said signal as a numerical value.

12. The invention according to claim 11 and said signal processing circuit including a detector circuit connected with the optical sensors and receiving therefrom said first signals, said detector circuit generating a pulse signal for each sensor representing pulse data derived from the respective first signal thereof.

13. The invention according to claim 12 and said signal processing circuit filtering said pulse signals to interrupt said pulse signal when the pulse signal indicates a pulse outside of predetermined limits.

14. The invention according to claim 11 and said display circuit including a supplemental signal processor processing said third signal prior to generating the display signal therefrom.

15. The invention according to claim 11 wherein said pulse detector unit has three optical sensors detecting blood in the wrist, said optical sensors being grouped adjacent each other in a generally triangular pattern.

16. A pulse monitoring system comprising:

a first band adapted to be engaged on a wrist of the user;

a detector unit supported on said first band and having thereon three optical detectors grouped together in a generally triangular pattern, said detectors each detecting time-varying amounts of blood in said wrist and each generating a respective responsive signal;

said detector unit transmitting a wireless signal derived from at least one of said responsive signals;

a display unit adapted to be supported on said wrist of the user, said display unit receiving said wireless signal and generating therefrom a display signal representing the pulse rate of the user;

the display unit having a display device receiving the display signal and displaying the display signal as a numerical value to be read by the user;

one of said detector unit and said display unit including a signal processing circuit processing one of said signals or a signal derived therefrom, said signal processing circuit;

a) interrupting the signal when the numerical value thereof is below a preselected minimum or above a preselected maximum;

b) interrupting the signal when the change in numerical value of said signal from the previous value of the signal exceeds a preselected value; and c) smoothing the values of said signal; and one of said detection unit and said display unit determining which of the responsive signals is transmitting the most reliable data and causing the data only of that signal to be used in generating the display signal.

17. The invention according to claim 16 and said display unit having a second band adapted to secure said display unit to the same wrist of the user as the first band.

18. The invention according to claim 16 and said detector unit having the signal processing circuit.

19. The invention according to claim 16 and said detection unit selecting the responsive signal having the most reliable data.

\* \* \* \* \*